United States Patent [19]

Draber et al.

[11] 4,282,388
[45] Aug. 4, 1981

[54] CYCLIC 1,2-DIOL BENZYL ETHER COMPOUNDS

[75] Inventors: Wilfried Draber; Wolf Reiser; Thomas Schmidt, all of Wuppertal; Ludwig Eue, Leverkusen; Robert R. Schmidt, Cologne, all of Fed. Rep. of Germany

[73] Assignee: Bayer Aktiengesellschaft, Leverkusen, Fed. Rep. of Germany

[21] Appl. No.: 964,415

[22] Filed: Nov. 28, 1978
(Under 37 CFR 1.47)

[30] Foreign Application Priority Data

Dec. 1, 1977 [DE] Fed. Rep. of Germany ....... 2753556
Sep. 28, 1978 [DE] Fed. Rep. of Germany ....... 2842188

[51] Int. Cl.³ .................. C07C 43/188; C07C 43/192
[52] U.S. Cl. ..................................... 568/660; 568/633; 568/636; 568/637; 568/643; 568/644; 568/645; 568/49; 71/124; 71/98; 71/106; 260/340.5 R; 560/60
[58] Field of Search ............... 568/660, 645, 644, 646, 568/638, 662, 633, 643, 636, 637

[56] References Cited

U.S. PATENT DOCUMENTS

| | | | |
|---|---|---|---|
| 2,500,016 | 3/1950 | Allenby et al. | 568/644 X |
| 2,812,358 | 11/1957 | Schlichting et al. | 568/660 X |
| 3,272,854 | 9/1966 | Covey et al. | 568/645 X |
| 3,377,384 | 4/1968 | Dorfman | 568/662 X |

FOREIGN PATENT DOCUMENTS 506 2/1979 European Pat. Off. ................. 568/638

1176120 11/1958 France .

OTHER PUBLICATIONS

Mamedov et al., C.A., vol. 59 (1963), 12654f-12655a.

*Primary Examiner*—Bernard Helfin
*Attorney, Agent, or Firm*—Sprung, Felfe, Horn, Lynch & Kramer

[57] ABSTRACT

Novel benzyl ethers of cyclic 1,1-diols, of the formula

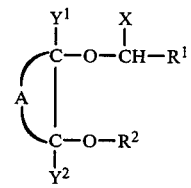

wherein
$R^1$ is phenyl or substituted phenyl,
$R^2$ is hydrogen, alkyl, alkenyl, alkynyl, haloalkyl or —CHX—$R^1$,
X is hydrogen, alkyl, alkenyl, alkynyl, haloalkyl, phenyl or substituted phenyl,
Y and Y' are individually selected from hydrogen, alkyl, phenyl and substituted phenyl and
A is saturated or unsaturated alkylene or substituted alkylene;

have been found outstandingly effective as herbicides, particularly as selective herbicides.

28 Claims, No Drawings

CYCLIC 1,2-DIOL BENZYL ETHER COMPOUNDS

The present invention relates to certain new benzyl ether compounds of cyclic 1,2-diols, to their use as herbicides and to herbicidal compositions containing such compounds.

It is already known that chloroacetanilides, for example 2-ethyl-6-methyl-N-(1'-methyl-2'methoxyethyl)-chloroacetanilide, can be used as herbicides, in particular for combating graminaceous weeds, from DT-OS (German-Published Specification) No. 2,328,340. However, these compounds are not always satisfactory in their selectivity.

The present invention now provides, as new compounds, benzyl ethers of cyclic 1,2-diols, of the general formula

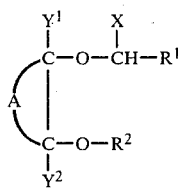

in which
R$^1$ is optionally substituted phenyl,
R$^2$ is hydrogen, alkyl, alkenyl, alkynyl, halogenoalkyl or the grouping —CHX—R$^1$,
X is hydrogen, alkyl, alkenyl, alkynyl, halogenoalkyl or optionally substituted phenyl,
Y$^1$ and Y$^2$, which are identical or different, each represent hydrogen, alkyl or optionally substituted phenyl and
A is optionally substituted, saturated or unsaturated alkylene.

These new benzyl ethers of cyclic 1,2-diols display powerful herbicidal, in particular selective herbicidal, properties.

Surprisingly, the benzyl ethers, according to the invention, of cyclic 1,2-diols are significantly superior in their herbicidal action to the previously known agents for combating grasses, such as, for example, 2-ethyl-6-methyl-N-(1'-methyl-2'-methoxyethyl)-chloroacetanilide, and in addition exhibit an excellent selectivity with important cultivated plants. The active compounds according to the invention thus represent a considerable enrichment of herbicidal agents, in particular of grass herbicides.

Preferably, A represents a two-membered to six-membered saturated or unsaturated alkylene bridge which optionally carries one or more substituents selected from halogen (especially chlorine or bromine), straight-chain or branched alkyl with 1 to 6 carbon atoms, a dimethylene, trimethylene, tetramethylene or pentamethylene bridge, phenyl and phenyl which is substituted by halogen, by alkyl or alkoxy with in either case 1 to 4 carbon atoms, or by halogenoalkyl, halogenoalkoxy or halogenoalkylthio with in each case up to 4 carbon atoms and up to 5 halogen atoms (especially with up to 2 carbon atoms and up to 3 identical or different halogen atoms, preferred halogens being fluorine, chlorine and bromine);

Y$^1$ and Y$^2$, which are identical or different, each represent hydrogen, straight-chain or branched alkyl with 1 to 6 carbon atoms or phenyl which is optionally substituted by halogen, alkyl or alkoxy with 1 to 4 carbon atoms or halogenoalkyl, halogenoalkoxy or halogenoalkylthio with in each case up to 4 carbon atoms and up to 5 halogen atoms (especially with up to 2 carbon atoms and up to 3 identical or different halogen atoms, preferred halogens being fluorine, chlorine and bromine);

R$^1$ represents phenyl which optionally carries one or more substituents selected from halogen (especially fluorine, chlorine or bromine), alkyl, alkoxy and alkylthio with in each case 1 to 4 carbon atoms, halogenoalkyl, halogenoalkoxy and halogenoalkylthio with in each case up to 4 carbon atoms and up to 5 halogen atoms (especially with up to 2 carbon atoms and up to 3 identical or different halogen atoms, preferred halogens being fluorine, chlorine and bromine), alkoxycarbonyl with 1 to 4 carbon atoms in the alkyl part, alkylamino and dialkylamino with 1 to 4 carbon atoms in each alkyl part, the methylenedioxy group, the trimethylene, tetramethylene or pentamethylene radical, and phenyl, phenoxy and phenoxycarbonyl, the last three radicals being optionally substituted by halogen (especially fluorine, chlorine or bromine), alkyl or alkoxy with in either case 1 to 2 carbon atoms or halogenoalkyl with up to 2 carbon atoms and up to 3 identical or different halogen atoms (especially fluorine and chlorine);

X represents hydrogen, straight-chain or branched alkyl with 1 to 4 carbon atoms, alkenyl or alkynyl with in either case 2 to 4 carbon atoms, halogenoalkyl with up to 2 carbon atoms and up to 3 identical or different halogen atoms (especially fluorine and chlorine), or phenyl which is optionally substituted by halogen, alkyl or alkoxy with in either case 1 or 2 carbon atoms or halogenoalkyl with up to 2 carbon atoms and up to 3 identical or different halogen atoms (especially fluorine and chlorine); and R$^2$ represents hydrogen, straight-chain or branched alkyl with 1 to 8 carbon atoms, alkenyl or alkynyl with in either case 2 to 4 carbon atoms, halogenoalkyl with up to 2 carbon atoms and up to 3 identical or different halogen atoms (especially fluorine and chlorine) or the grouping —CHX—R$^1$ wherein R$^1$ and X have the meanings stated immediately above.

The compounds of the formula (I) can in each case exist in the form of geometric isomers, that is to say in the form of cis-isomers and in the form of trans-isomers, and as mixtures of these two isomers. Moreover, most of these compounds in each case also exist as optical isomers. The formula (I) embraces all the isomers.

The present invention also provides a process for the preparation of a benzyl ether of the formula (I), of a cyclic 1,2-diol, in which a cyclic 1,2-diol of the general formula

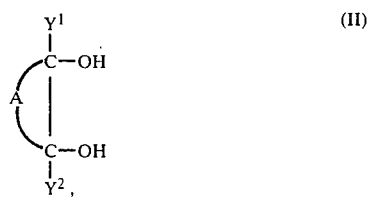

in which A, Y$^1$ and Y$^2$ have the meanings stated above, is reacted with a compound of the general formula

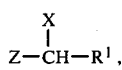 (III)

in which
R¹ and X have the meanings stated above and
Z represents halogen (especially chlorine, bromine or iodine) or the mesylate or tosylate radical, in the presence of a strong base and in the presence of a diluent, and the benzyl ether formed of the general formula

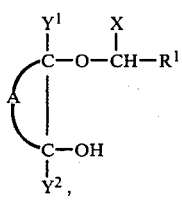 (IV)

in which A, R¹ X, Y¹ and Y² have the meanings stated above, is optionally reacted with a compound of the formula

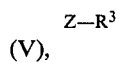 (V), in which
Z has the meaning stated above and
R³ represents alkyl, alkenyl, alkynyl, halogenoalkyl or the grouping —CHX—R¹,
wherein
R¹ and X have the meanings stated above, in the presence of a strong base and in the presence of a diluent (process variant (A)).

In some cases it proves to the advantageous first to react a cyclic 1,2-diol of the formula (II) with a compound of the formula (V) and then to react the ether formed of the general formula

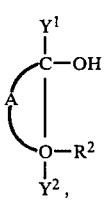 (VI)

in which A, R², Y¹ and Y² have the meanings stated above, with a compound of the formula (III) (process variant (B)).

If cis-1,2-cyclobutanediol, 2-fluorobenzyl chloride and methyl iodide are used as starting materials and sodium hydroxide is used as the strong base according to process variant (A), the course of the reaction can be represented by the following equation:

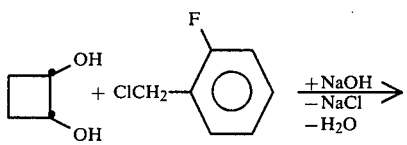

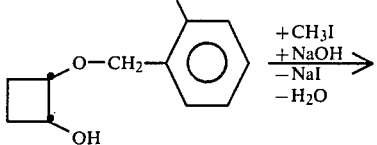

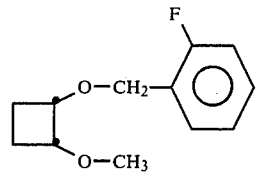

If trans-1,2-dimethyl-cyclohexane-1,2-diol, ethyl bromide and 2,4-dichlorobenzyl chloride are used as the starting materials and potassium hydroxide is used as the strong base according to process variant (B), the course of the reaction can be represented by the following equation:

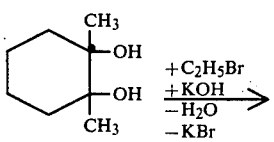

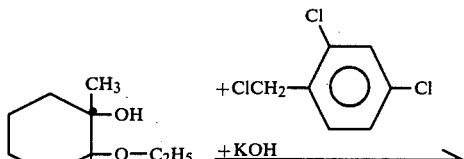

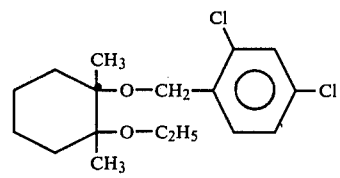

The cyclic 1,2-diols of the formula (II) are known (see Tetrahedron Letters 1972, 857–860; F. D. Gunstone in Advances in Organic Chemistry, Methods and Results, volume 1, Interscience Publishers, New York (1960); and J.Am.Chem. Soc. 56, 1993 (1934)) or can be prepared by known methods. They are obtained, for example, by a process in which 1,2-bis-(trimethylsiloxy)-cycloalkenes of the general formula

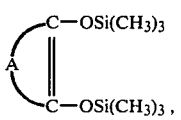 (VII)

in which A has the meaning stated above,
(a) are hydrogenated with hydrogen in the presence of a catalyst, such as, for example, palladium-on-charcoal, at a temperature of 20°–80° C. and under a pressure of 80–100 atmospheres and the cis-1,2-bis-(trimethylsiloxy)-cycloalkanes formed, of the formula

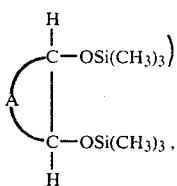
(VIII)

in which A has the meaning stated above, are hydrolysed in the customary manner (see Tetrahedron Letters 1972, 857–860), or (b) are subjected to acid hydrolysis or alcoholysis (see K. Rühlmann, Synthesis 1971, 236) and the cyclic α-hydroxyketones formed, of the formula

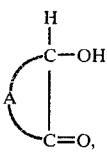
(IX)

in which A has the meaning stated above, are reduced in the customary manner with complex hydrides, for example sodium borohydride, in the presence of a polar organic solvent, for example an alcohol, at temperatures between 0° and 30° C. or are reacted with Grignard reagents in the presence of anhydrous ethers as diluents at temperatures between 30° and 60° C. (see J.Am. Chem. Soc. 56, 1993 (1934)).

The cyclic 1,2-diols of the formula (II) can also be obtained when (c) cycloalkenes of the general formula

(X)

in which A, $Y^1$ and $Y^2$ have the meanings stated above, are oxidized in the customary manner with potassium permanganate or osmium tetroxide at temperatures between −80° C. and room temperature (see F. D. Gunstone in Advances in Organic Chemistry, Methods and Results, volume 1, Interscience Publishers, New York (1960)). The oxidation can also be carried out under phase transfer catalysis (see Tetrahedron Letters 1972, 4907-8).

The 1,2-bis-(trimethylsiloxy)-cycloalkenes of the formula (VII) to be used as starting materials are known from K. Rühlmann, Synthesis 1971, 236, or can be prepared by the processes described therein, for example by reacting dicarboxylic acid esters with sodium in inert solvents, trimethylchlorosilane being added.

The cyclic α-hydroxy-ketones of the formula (IX) can also be obtained by oxidizing corresponding epoxides with dimethylsulphoxide, optionally in the presence of a catalyst, such as, for example, boron trifluoride (see J. Org. Chem. 26, 1681 (1961)).

The cycloalkenes of the formula (X) to be used as starting materials are generally known compounds of organic chemistry.

Examples which may be mentioned of the cyclic 1,2-diols of the formula (II) to be used as starting materials are: cyclobutane-1,2-diol, cyclopentane-1,2-diol, cyclohexane-1,2-diol, cycloheptane-1,2-diol, cyclooctane-1,2-diol, 1-methyl-cyclobutane-1,2-diol, 1-methyl-cyclopentane-1,2-diol, 1-methyl-cyclohexane-1,2-diol, 1-methyl-cycloheptane-1,2-diol, 1-methyl-cyclooctane-1,2-diol, 1-ethyl-cyclobutane-1,2-diol, 1-ethyl-cyclopentane-1,2-diol, 1-ethyl-cyclohexane-1,2-diol, 3,4-tetramethylene-cyclobutane-1,2-diol, cyclohex-4-ene-1,2-diol, 1,2-dimethyl-cyclobutane-1,2-diol, 1,2-dimethyl-cyclohexane-1,2-diol, 1,2-dimethyl-cycloheptane-1,2-diol, 1,2-dimethyl-cyclooctane-1,2-diol, 1-phenyl-cyclobutane-1,2-diol, 1-phenyl-cyclopentane-1,2-diol, 1-phenylcyclohexane-1,2-diol, 1-phenyl-cycloheptane-1,2-diol, 3-methyl-cyclobutane-1,2-diol, 3-ethyl-cyclobutane-1,2-diol, 3-isopropyl-cyclobutane-1,2-diol, 3-tert.-butyl-cyclobutane-1,2-diol and 3,3-dimethyl-cyclobutane-1,2-diol.

The starting materials of the formula (III) are generally known compounds of organic chemistry. Examples which may be mentioned are: benzyl chloride, benzyl bromide, benzyl iodide, benzyl mesylate, benzyl tosylate, 2-fluorobenzyl iodide, 2-fluorobenzyl bromide, 3-fluorobenzyl bromide, 4-fluorobenzyl bromide, 3-chlorobenzyl chloride, 4-chlorobenzyl chloride, 2-bromobenzyl chloride, 3-bromobenzyl chloride, 4-bromobenzyl chloride, 2-methylbenzyl chloride, 3-methylbenzyl chloride, 4-methylbenzyl chloride, 2-methoxybenzyl chloride, 3-methoxybenzyl chloride, 4-methoxybenzyl chloride, 2-trifluoromethylbenzyl chloride, 3-trifluoromethylbenzyl chloride, 4-trifluoromethylbenzyl chloride, 4-phenylbenzyl chloride, 2,6-difluorobenzyl chloride, 2,6-dichlorobenzyl chloride, 2,4-dichlorobenzyl chloride, 3,4-dichlorobenzyl chloride, 2,5-dichlorobenzyl chloride, 2,6-dimethylbenzyl chloride, 2,4-dimethylbenzyl bromide, 3,4-dimethylbenzyl chloride, 2,3-dimethylbenzyl chloride, 3,4-dioxymethylenebenzyl chloride, 2,6-chlorofluorobenzyl chloride, 2-fluoro-5-chlorobenzyl bromide, 2-fluoro-4-chlorobenzyl bromide, 3-chloro-4-fluorobenzyl bromide, 3,4-tetramethylenebenzyl chloride, 2-methyl-6-chlorobenzyl chloride, 2-methyl-6-fluorobenzyl chloride, 2-fluoro-3-methylbenzyl chloride, 2-fluoro-4-methylbenzyl chloride, 2-fluoro-5-methylbenzyl chloride, 2-methyl-3-chlorobenzyl chloride, 2-methyl-4-chlorobenzyl chloride, 2-methyl-5-chlorobenzyl chloride, 2,4,5-trichlorobenzyl bromide, 2,4,6-trichlorobenzyl bromide, diphenylmethyl bromide, 1-bromo-1-phenylethane and 1-bromo-1-(2-methylphenyl)ethane.

The starting materials of the formula (V) are generally known compounds of organic chemistry. Examples which may be mentioned are: methyl chloride, methyl bromide, methyl iodide, ethyl bromide, n-propyl bromide, isopropyl bromide, tert.-butyl iodide, allyl bromide, allyl iodide, vinyl bromide, buten-2-yl chloride, propargyl chloride and the examples of compounds of the formula (III) which have already been mentioned.

The possible intermediate products of the formula (VI) are known, in some cases, from J. Chem. Soc. (London) 1964, 2846-8, and they can also be prepared by the processes indicated therein. They are likewise obtained when corresponding o-alkoxyphenols are hydrogenated in the customary manner in the presence of a catalyst.

Preferred diluents for the reaction according to the invention are inert organic solvents, especially ethers, such as diethyl ether, tetrahydrofuran or dioxan; aromatic hydrocarbons, such as benzene or toluene; and in individual cases also chlorinated hydrocarbons, such as chloroform, methylene chloride or carbon tetrachloride, as well as dimethylsulphoxide.

The reaction according to the invention is carried out in the presence of a strong base. Preferred strong bases are alkali metal hydrides, amides, hydroxides and carbonates, for example sodium hydride, sodium amide, sodium hydroxide, potassium hydroxide and potassium carbonate.

The reaction temperatures in the process according to the invention can be varied within a relatively wide range. In general, the reaction is carried out at from 0° to 120° C., preferably at from 20° to 100° C.

In carrying out the process according to the invention, equimolar amounts of the reactants are preferably used, although it can be advantageous in some cases to employ the base and the compounds of the formula (V) each in an excess of up to 1.5 moles.

In order to isolate the end products, water is added to the reaction mixture, an organic solvent is added, if appropriate, and the organic phase is separated off and worked up and purified in the customary manner.

According to a preferred embodiment, the reaction according to the invention is carried out in a two-phase system, for example, aqueous sodium hydroxide solution or potassium hydroxide solution/toluene or methylene chloride, a phase transfer catalyst, for example an ammonium compound such as triethyl-benzyl-ammonium chloride or tetra-n-butylammonium chloride or bromide, being added.

Examples which may be mentioned of particularly active compounds according to the invention (in addition to those given in the preparative Examples later in this text) are: 1,2-bis(2-fluorobenzyloxy)-cyclobutane, 1-(2-fluorobenzyloxy)-2-methoxy-2-methyl-cyclobutane, 1-(2-fluorobenzyloxy)-2-methoxy-2-methyl-cyclopentane, 1-(2-fluorobenzyloxy)-2-methoxy-2-methyl-cyclohexane, 1-(2-fluorobenzyloxy)-2-methoxy-2-methyl-cycloheptane, 1-(2-fluorobenzyloxy)-2-methoxy-2-methyl-cyclooctane, 1,2-bis-(2-fluorobenzyloxy)-1-ethyl-cyclopentane and 1-(2-fluorobenzyloxy)-2-ethyl-2-methoxy-cyclopentane.

The active compounds according to the invention influence plant growth and can therefore be used as defoliants, desiccants, agents for destroying broad-leaved plants and germination inhibitors, and especially as weedkillers. By "weeds", in the broadest sense, there are meant plants growing in locations where they are not desired. Whether the compounds according to the invention act as total or selective herbicides depends essentially on the amount used.

The active compounds according to the invention can be used, for example, to combat the following plants:

dicotyledon weeds of the genera: Sinapis, Lepidium, Galium, Stellaria, Matricaria, Anthemis, Galinsoga, Chenopodium, Urtica, Senecio, Amaranthus, Portulaca Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea; and monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monocharia, Fimbristylis, Sagittaria, Eleocharis, Scirpus, Paspalum, Ischaemum, Spenoclea, Datyloctenium, Agrostis, Alopecurus and Apera.

The active compounds according to the present invention may be used, for example, as selective herbicides in the following cultures:

dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita; and monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds can be used, depending on the concentration, for the total combating of weeds, for example on industrial terrain and rail tracks, and on paths and squares with or without tree plantings. Equally, the compounds can be employed for combating weeds in perennial cultures, for example forestry plantations, decorative tree plantings, orchards, vineyards, citrus groves, nut orchards, banana plantations, coffee plantations, tea plantations, rubber plantations, oil palm plantations, cacao plantations, soft fruit plantings and hopfields, and for the selective combating of weeds in annual cultures.

The active compounds according to the invention are preferably employed for the selective combating of weeds, and especially of wild grasses, in various crops. Using the active compounds according to the invention it is possible—in contrast to the chloroacetanilides known as grass herbicides—successfully to combat Alopercurus or Poa annua, which are wild grasses difficult to combat, simultaneously with other harmful grasses, for example Digitaria, Echinochloa, Panicum or Setaria, in crops such as sugar beet, soya beans, cotton, rape, groundnuts, various vegetables, maize and rice.

The active compounds can be converted into the customary formulations, such as solutions, emulsions, wettable powders, suspensions, powders, pastes, soluble powders, granules, suspension-emulsion concentrates, foams, natural and synthetic materials impregnated with active compound, very fine capsules in polymeric substances.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95% by weight of active compound, preferably from 0.5 to 90% by weight. The active compounds according to the invention, as such or in the form of their formulations, can also be used for combating weeds as mixtures with known herbicides, finished formulations or tank mixing being possible. Mixtures with other active compounds, such as fungicides, insecticides, acaricides, nematicides, substances affording protection against damage caused by birds, growth factors, plant nutrients and agents which improve the structure of the soil, are also possible.

The active compounds can be used as such, as their formulations or as the use forms prepared therefrom by further dilution, such as ready-to-use solutions, emulsions, suspensions, powders, pastes and granules. They may be used in the customary manner, for example by watering, spraying, atomising, dusting or scattering.

The active compounds according to the invention can be applied after or, preferably, before emergence of the plants. They can also be incorporated into the soil before sowing.

The amount of active compound used can vary within relatively wide limits. It depends essentially on the nature of the desired effect. In general, the amounts used are from 0.1 to 10 kg of active compound per hectare, preferably from 0.1 to 5 kg/ha.

The present invention also provides a herbicidal composition containing as active ingredient a compound of the present invention in admixture with a solid or liquefied gaseous diluent or carrier or in admixture with a liquid diluent or carrier containing a surface-active agent.

The present invention also provides a method of combating weeds which comprises applying to the weeds, or to a habitat thereof, a compound of the present invention alone or in the form of a composition containing as active ingredient a compound of the present invention in admixture with a diluent or carrier.

The present invention further provides crops protected from damage by weeds by being grown in areas in which immediately prior to and/or during the time of the growing a compound of the present invention was applied alone or in admixture with a diluent or carrier.

It will be seen that the usual methods of providing a harvested crop may be improved by the present invention.

The herbicidal activity of the compounds of this invention is illustrated by the following biotest Example.

EXAMPLE A

Pre-emergence test

Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

Seeds of the test plants were sown in normal soil and, after 24 hours, watered with the preparation of active compound. It was expedient to keep constant the amount of water per unit area. The concentration of the active compound in the preparation was of no importance, only the amount of active compound applied per unit area being decisive. After three weeks, the degree of damage to the plants was rated in % damage in comparison to the development of the untreated control. 0% denoted no action (as for the untreated control) and 100% denoted total destruction.

In this test, for example, the following compounds showed an excellent action which was significantly superior to the action of the compounds of the same type of action known from the prior art: the compounds from preparative Examples 1, 6, 30, 31 and 61.

PREPARATIVE EXAMPLES

EXAMPLE 1

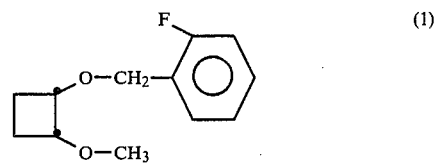

(1)

396.0 g. (4.5 mol) of cis-1,2-cyclobutanediol and 650.3 g (4.5 mol) of 2-fluorobenzyl chloride were dissolved in 2.5 liters of dimethylsulphoxide, and 270 g (6.75 mol) of sodium hydroxide powder were added in portions at room temperature, whilst cooling with ice. The mixture was stirred at room temperature for 6 hours and 958.5 g (6.75 mol) of methyl iodide and, in portions, 270 g (6.75 mol) of sodium hydroxide powder were then added, whilst cooling. Thereafter, the reaction mixture was again stirred at room temperature for 6 hours and discharged onto 10 liters of ice-water. The mixture was extracted three times with 5 liters of petroleum ether each time and the combined organic phases were dried over sodium sulphate and concentrated by distilling off the solvent. 840 g (88.9% of theory) of cis-1-(2-fluorobenzyloxy)-2-methoxy-cyclobutane of refractive index $n_D^{21} = 1.4948$ were obtained.

The starting material cis-1,2-cyclobutanediol was prepared by catalytic hydrogenation of 1,2-bis-(trimethylsiloxy)-cyclobut-1-ene to cis-1,2-bis-(trimethylsiloxy)-cyclobutane and hydrolysis thereof, according to Tetrahedron Letters 9, 857-860 (1972).

EXAMPLE 2

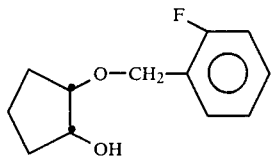 (2)

19.4 g (0.19 mol) of cis-1,2-cyclopentanediol were added dropwise to a suspension of 4.8 g (0.2 mol) of sodium hydride (6.0 g of 80% pure sodium hydride in toluene) in 200 ml of dioxan at 5° C. under a nitrogen atmosphere, whilst stirring. After the evolution of hydrogen had ended, the mixture was warmed to 70° C. for 45 minutes and then brought to room temperature and 359 g (0.19 mol) of 2-fluorobenzyl bromide in absolute dioxan were added. After stirring the mixture for 30 minutes, it was heated to the boil for a further 4 hours and cooled and about 10 ml of methanol were added. The mixture was concentrated to dryness on a rotary evaporator, the residue was taken up in water and the mixture was extracted with methylene chloride. The organic phase was dried over sodium sulphate and filtered and the solvent was stripped off from the filtrate on a rotary evaporator. The oily residue was distilled under an oil pump vacuum. 18.4 g (46% of theory) of cis-1-(2-fluorobenzyloxy)-cyclopentan-2-ol of boiling point 95°-100° C./0.1 mm Hg were obtained.

Preparation of the starting material

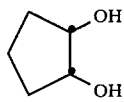

A solution of 1,000 ml of tert.-butanol, 200 ml of water, 500 g of crushed ice and 7 g (0.1 mol) of cyclopentene was cooled to −10° C. A solution, cooled to 0° C., of 20.5 g (0.13 mol) of potassium permanganate and 4 g (0.1 mol) of sodium hydroxide was added to this solution in the course of 5 minutes and the mixture was stirred at 0° C. for 5 minutes. A solution of 0.05 mol of sodium sulphite in 50 ml of water was then added dropwise, the manganese dioxide was filtered off and the tert.-butanol was distilled off. The solution was then concentrated to about 200 ml on a rotary evaporator and the concentrate was extracted several times with ether. The combined ether phases were dried over sodium sulphate and filtered, the solvent was stripped off from the filtrate and the residue was distilled. 3.4 g (33% of theory) of cis-1,2-cyclopentanediol of boiling point 114° C./12 mm Hg were obtained.

EXAMPLE 3

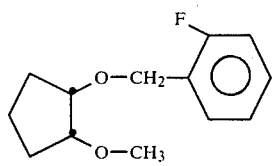 (3)

6.3 g (0.03 mol) of cis-1-(2-fluorobenzyloxy)-cyclopentan-2-ol (Example 2) in 100 ml of absolute dioxan were added dropwise to a suspension of 0.72 g (0.03 mol) of sodium hydride (0.9 g of 80% pure sodium hydride in toluene) in 100 ml of absolute dioxan at 5° C. under nitrogen. After stirring the mixture at room temperature for 30 minutes, it was warmed to 70° C. for 45 minutes and cooled, 1.26 g (0.03 mol) of methyl iodide in dioxan were added dropwise and the mixture was then heated to the boil for 4 hours. After cooling the mixture to room temperature, 5 ml of methanol were added dropwise and the suspension was concentrated on a rotary evaporator. The residue was taken up in water and the mixture was extracted again with methylene chloride. The combined methylene chloride phases were dried over sodium sulphate and filtered and the solvent was stripped off from the filtrate on a rotary evaporator. The oily residue was distilled. 5 g (75% of theory) of cis-1-(2-fluorobenzyloxy)-2-methoxy-cyclopentane of boiling point 90° C./0.1 mm Hg were obtained.

EXAMPLE 4

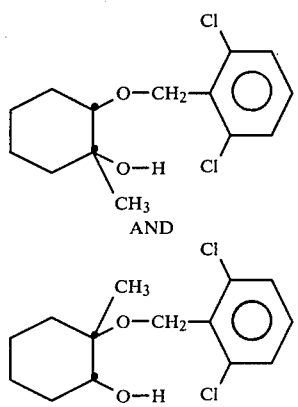

A solution of 3.9 g (0.03 mol) of cis-1-methyl-cyclohexane-1,2-diol was added dropwise, in a stream of nitrogen, to a suspension of 0.72 g (0.03 mol) of sodium hydride (0.9 g of 80% pure sodium hydride in toluene) in 100 ml of absolute dioxan, whilst cooling. After the evolution of hydrogen had ended, the mixture was warmed to 70° C. for 30 minutes and, after cooling, 5.9 g (0.03 mol) of 2,6-dichlorobenzyl chloride were added dropwise. After stirring the mixture at room temperature for 30 minutes, it was heated under reflux for 4 hours and, after cooling, 5 ml of methanol were added and the mixture was concentrated to dryness on a rotary evaporator. The residue was taken up in water and the mixture was again extracted with methylene chloride. The combined organic phases were dried over sodium sulphate and filtered and the solvent was stripped off from the filtrate on a rotary evaporator.

The oily residue was distilled. 7 g (81% of theory) of a mixture of cis-1-(2,6-dichlorobenzyloxy)-2 (and 1)-methyl-cyclohexan-2-ol of boiling point 135°–138° C./0.1 mm Hg were obtained.

Preparation of the starting material

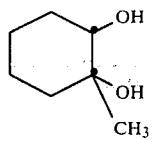

38.8 g (0.34 mol) of 2-hydroxycyclohexanone in ether were added dropwise to a solution of 116.2 g (0.7 mol) of methyl-magnesium iodide in ether, whilst stirring. After the reaction had ended, the suspension was poured onto a mixture of water, ether and dilute sulphuric acid, the ether phase was separated off and the aqueous phase was extracted several times with ether. The combined ether extracts were dried over sodium sulphate, the solvent was stripped off on a rotary evaporator and the residue was distilled. 21.2 g (48% of theory) of 1-methyl-cyclohexane-1,2-diol of boiling point 75° C./0.2 mm Hg, which was present in the cis-form to the extent of >90%, were obtained.

Preparation of the precursor

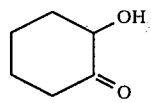

0.4 ml of boron trifluoride-etherate was added to 98 g (1 mol) of cyclohexene oxide in 200 ml of absolute dimethylsulphoxide and the mixture was heated to 120° C. for 22 hours, whilst stirring. After 10 hours and 20 hours, in each case a further 0.2 ml of boron trifluoride-etherate was added. After cooling, the reaction mixture was poured onto ice and the aqueous solution was extracted with chloroform. The organic phase is dried over sodium sulphate and filtered and the solvent was stripped off from the filtrate on a rotary evaporator. The residue was distilled under a waterpump vacuum. 88.4 g (68% of theory) of 2-hydroxy-cyclohexanone of boiling point 83°–85° C./12 mm Hg were obtained.

EXAMPLE 5

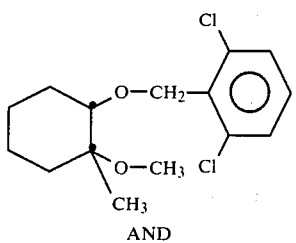

AND

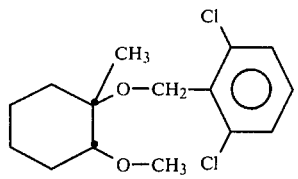

8.7 g (0.03 mol) of a mixture of cis-1-(2,6-dichlorobenzyloxy)-2 (and 1)-methyl-cyclohexan-2-ol (Example 4) in 100 ml of absolute dioxan were added dropwise to a suspension of 0.72 g (0.03 mol) of sodium hydride (0.9 g of 80% pure sodium hydride in toluene) in 100 ml of absolute dioxan at 5° C. under a nitrogen atmosphere. After stirring the mixture at room temperature for 30 minutes, it was warmed to 70° C. for 45 minutes and, after cooling, 4.26 g (0.03 mol) of methyl iodide were added. The mixture was stirred at room temperature for 30 minutes and then heated to the boil for 4 hours. After cooling, about 5 ml of methanol were added and the mixture was concentrated on a rotary evaporator. The residue was taken up in water and the aqueous phase was extracted several times with methylene chloride. The combined organic phases were dried over sodium sulphate and filtered, the solvent was stripped off from the filtrate on a rotary evaporator and the oily residue was distilled. 5 g (55% of theory) of a mixture of cis-1-(2,6-dichlorobenzyloxy)-2-methoxy-2 (and 1)-methyl-cyclohexane of boiling point 131° C./0.1 mm Hg were obtained.

EXAMPLE 6

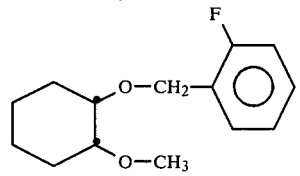

772 g (19.3 mol) of sodium hydroxide powder were added in portions to 1,672 g (12.8 mol) of cis-2-methoxycyclohexanol and 1,853 g (12.8 mol) of 2-fluorobenzyl chloride in 10 l of dimethylsulphoxide, whilst cooling with water. The mixture was stirred at 35° C. for 2 hours and at 45° C. overnight. Thereafter, it was cooled to 18° C., 10 l of petroleum ether were added and the mixture was discharged onto 10 ml of ice-water. The organic phase was separated off, extracted by shaking with water, dried over sodium sulphate and filtered and the filtrate was concentrated. The oily residue was distilled. 2,685 g (87.5% of theory) of cis-1-(2-fluorobenzyloxy)-2-methoxy-cyclohexane of boiling point 150° C./2 mm Hg were obtained.

The starting material cis-2-methoxy-cyclohexanol was prepared according to J. Chem. Soc. (London) 1964, 2846–8.

The compounds listed in Table 1 which follows were prepared in an analogous manner.

TABLE 1

$$\begin{array}{c} Y^1 \quad X \\ C-O-CH-R^1 \\ A \mid \\ C-O-R^2 \\ Y^2 \end{array} \quad (I)$$

| Ex. No. | R¹ | R² | X | Y¹ | Y² | A | Boiling point (°C./mm Hg) |
|---|---|---|---|---|---|---|---|
| 7 | phenyl | CH₃ | H | H | H | —(CH₂)₄— | 155/20 (trans) |
| 8 | 2-Cl-phenyl | CH₃ | H | H | H | —(CH₂)₄— | 180/20 (trans) |
| 9 | 4-Cl-phenyl | CH₃ | H | H | H | —(CH₂)₄— | 142/0,2 (trans) |
| 10 | 3,4-diCl-phenyl | CH₃ | H | H | H | —(CH₂)₄— | 125/0,1 (trans) |
| 11 | 2-CF₃-phenyl | CH₃ | H | H | H | —(CH₂)₄— | 125/0,1 (trans) |
| 12 | 2-F-phenyl | CH₃ | H | H | H | —(CH₂)₄— | 120/0,2 (trans) |
| 13 | 2,4-diCl-phenyl | CH₃ | H | H | H | —(CH₂)₄— | 200/0,5 (trans) |
| 14 | 2-CH₃-phenyl | CH₃ | H | H | H | —(CH₂)₃— | 95/0,1 (trans) |
| 15 | 2-CH₃-phenyl | CH₃ | H | H | H | —(CH₂)₄ | 115/0,1 (trans) |
| 16 | 4-CF₃-phenyl | CH₃ | H | H | H | —(CH₂)₃— | 85/0,1 (trans) |
| 17 | 2,4-diCl-phenyl | CH₃ | H | H | H | —(CH₂)₃— | 110/0,1 (trans) |
| 18 | 2-Cl-phenyl | CH₃ | H | H | H | —(CH₂)₃— | 115-25/0,2 (trans) |
| 19 | 3-CH₃-phenyl | CH₃ | H | H | H | —(CH₂)₄— | 125/0,1 (trans) |
| 20 | 2-F-phenyl | CH₃ | H | H | H | —(CH₂)₃— | 85/0,2 (trans) |
| 21 | 3-CF₃-phenyl | CH₃ | H | H | H | —(CH₂)₄— | 90/0,05 (trans) |
| 22 | 3-F-phenyl | CH₃ | H | H | H | —(CH₂)₄— | 120-40/0,1 (trans) |
| 23 | 4-F-phenyl | CH₃ | H | H | H | —(CH₂)₄— | 120-30/0,1 (trans) |

TABLE 1-continued $$\begin{array}{c} Y^1 \quad X \\ \overset{|}{C}-O-\overset{|}{C}H-R^1 \\ A\overset{\phantom{|}}{\underset{|}{\diagup}} \\ C-O-R^2 \\ \overset{|}{Y^2} \end{array} \quad (I)$$

| Ex. No. | R¹ | R² | X | Y¹ | Y² | A | Boiling point (°C./mm Hg) |
|---|---|---|---|---|---|---|---|
| 24 | 3-CF₃, 4-Cl-phenyl | CH₃ | H | H | H | —(CH₂)₄— | 130/0,1 (trans) |
| 25 | 2-Cl-phenyl | CH₃ | H | H | H | —(CH₂)₂— | 120/0,1 (cis) |
| 26 | 4-F-phenyl | CH₃ | H | H | H | —(CH₂)₂— | 110/0,1 (cis) |
| 27 | 3-Cl, 4-OCF₃-phenyl | CH₃ | H | H | H | —(CH₂)₄— | 120/0,1 (trans) |
| 28 | 4-OCF₃-phenyl | CH₃ | H | H | H | —(CH₂)₄— | 130–50/0,1 (trans) |
| 29 | phenyl | CH₃ | H | H | H | —(CH₂)₂— | 80/0,1 (cis) |
| 30 | CH₃, 2-CH₃-phenyl | CH₃ | H | H | H | —(CH₂)₂— | 110/0,1 (cis) |
| 31 | Br, 2-Br-phenyl | CH₃ | H | H | H | —(CH₂)₂— | 130/0,1 (cis) |
| 32 | Br, 2-Br-phenyl | —CH₂-(2-Br-phenyl) | H | H | H | —(CH₂)₂— | 180/0,1 (cis) |
| 33 | 3-CH₃-phenyl | CH₃ | H | H | H | —(CH₂)₂— | 120/0,1 (cis) |
| 34 | 3-CH₃-phenyl | —CH₂-(3-CH₃-phenyl) | H | H | H | —(CH₂)₂— | 160/0,1 (cis) |
| 35 | phenyl | CH₃ | H | H | H | —(CH₂)₄— | 92/0,1 (cis/trans) |
| 36 | phenyl | —CH₂-phenyl | H | H | H | —(CH₂)₄— | 152–57/0,1 (cis/trans) |
| 37 | CH₃, 2-CH₃-phenyl | CH₃ | H | H | H | —(CH₂)₄— | 105–10/0,1 (cis/trans) |
| 38 | CH₃, 3-CH₃-phenyl | —CH₂-(3-CH₃-phenyl) | H | H | H | —(CH₂)₄— | 156–60/0,1 (cis/trans) |
| 39 | 2-Cl, 4-Cl-phenyl | CH₃ | H | H | H | —(CH₂)₄— | 150/0,1 (cis) |
| 40 | CH₃, 2-CH₃-phenyl | CH₃ | H | H | H | —(CH₂)₄— | 100/0,1 (cis) |
| 41 | 4-F-phenyl | CH₃ | H | H | H | —(CH₂)₄— | 115/0,2 (cis) |

TABLE 1-continued $$\begin{array}{c} Y^1 \quad X \\ | \quad | \\ C-O-CH-R^1 \\ A \Big| \\ C-O-R^2 \\ | \\ Y^2 \end{array} \quad (I)$$

| Ex. No. | R¹ | R² | X | Y¹ | Y² | A | Boiling point (°C./mm Hg) |
|---|---|---|---|---|---|---|---|
| 42 | Br—C₆H₄— | CH₃ | H | H | H | —(CH₂)₄— | 170/0,1 (cis) |
| 43 | 2,3-Cl₂—C₆H₃— | CH₃ | H | H | H | —(CH₂)₄— | 135/0,1 (cis) |
| 44 | C₆H₅— | —CH₂—C₆H₅ | H | H | H | —(CH₂)₂— | 150/0,7 (cis) |
| 45 | C₆H₅— | H | H | H | H | —(CH₂)₄— | 110/0,2 (cis) |
| 46 | C₆H₅— | CH₃ | H | H | H | (CH₂)₄⟨CH₂—⟩CH₂— | 120/0,1 (cis) |
| 47 | C₆H₅— | n-C₄H₉ | H | H | H | —(CH₂)₄— | 125/0,2 (cis) |
| 48 | F—C₆H₄— | C₂H₅ | H | H | H | —(CH₂)₄— | 120/0,2 (cis) |
| 49 | F—C₆H₄— | i-C₃H₇ | H | H | H | —(CH₂)₄— | 125/0,2 (cis) |
| 50 | Cl—C₆H₄— | i-C₃H₇ | H | H | H | —(CH₂)₄— | 130/0,2 (cis) |
| 51 | F—C₆H₄— | H | H | H | H | —(CH₂)₄ | 115/0,1 (cis) |
| 52 | F—C₆H₄— | —CH₂—CH=CH₂ | H | H | H | —(CH₂)₄— | 125/0,2 (cis) |
| 53 | 2,3-Cl₂—C₆H₃— | i-C₃H₇ | H | H | H | —(CH₂)₄— | 150/0,2 (cis) |
| 54 | 3-C₆H₅O—C₆H₄— | CH₃ | H | H | H | —(CH₂)₄— | 190/0,2 (cis) |
| 55 | Cl—C₆H₄— | CH₃ | H | H | H | —(CH₂)₄— | 125/0,2 (cis) |
| 56 | Cl—C₆H₄— | CH₃ | H | H | H | —(CH₂)₅— | 134/0,15 (trans) |
| 57 | F—C₆H₄— | CH₃ | H | H | H | —(CH₂)₅— | 112/0,2 (trans) |

TABLE 1-continued $$\underset{Y^2}{\overset{Y^1}{\underset{C-O-R^2}{\overset{C-O-CH-R^1}{A}}}}\quad\quad (I)$$

| Ex. No. | R¹ | R² | X | Y¹ | Y² | A | Boiling point (°C./mm Hg) |
|---|---|---|---|---|---|---|---|
| 58 | F-phenyl | -CH₂-phenyl-F | H | H | H | —(CH₂)₃— | 153/0,1 (cis) |
| 59 | Cl-phenyl | -CH₂-phenyl-Cl | H | H | H | —(CH₂)₃— | 185/0,2 (cis) |
| 60 | Cl-phenyl | -CH₂-phenyl-Cl | H | H | H | —(CH₂)₃— | Oil (cis/trans) |
| 61 | F-phenyl | C₂H₅ | H | H | H | —(CH₂)₃— | 94/0,1 (cis) |
| 62 | F-phenyl | -CH₂-phenyl-F | H | H | H | —(CH₂)₅— | 159/0,1 (cis) |
| 63 | F-phenyl | -CH₂-phenyl-F | H | H | C₂H₅ | —(CH₂)₃— | 145/0,1 (cis) |
| 64 | F-phenyl | H | H | H | H | —(CH₂)₅— | 109/0,1 (cis) |
| 65 | phenyl | H | H | H | C₂H₅ | —(CH₂)₃— | 97/0,1 (cis) |
| 66 | F-phenyl | CH₃ | H | H | H | —(CH₂)₅— | 99/0,1 (cis) |
| 67* | F-phenyl | CH₃ | H | H (C₂H₅) | C₂H₅ (H) | —(CH₂)₃— | 109/0,1 (cis)* |
| 68 | CH₃-phenyl | CH₃ | H | H | H | —(CH₂)₃— | 102/0,1 (cis) |
| 69 | CH₃-phenyl | CH₃ | H | H | H | —(CH₂)₅— | 115–30/0,06 (cis) |
| 70 | Cl-phenyl | CH₃ | H | H | H | —(CH₂)₅— | 135–48/0,1 (cis) |
| 71 | Cl-phenyl-Cl | CH₃ | H | H | H | —(CH₂)₅— | 136–47/0,05 (cis/trans) |
| 72 | Cl-phenyl-Cl | CH₃ | H | H | H | —(CH₂)₃— | 129/0,3 (cis) |
| 73 | Cl,Cl-phenyl | -CH₂-phenyl-Cl,Cl | H | H | H | —(CH₂)₃— | 205–15/0,1 (cis) |

TABLE 1-continued $$\overset{A}{\underset{}{\left\langle\begin{array}{c}\overset{Y^1}{\underset{}{C}}-O-\overset{X}{\underset{}{CH}}-R^1\\ \underset{Y^2}{\overset{}{C}}-O-R^2\end{array}\right.}} \tag{I}$$

| Ex. No. | R¹ | R² | X | Y¹ | Y² | A | Boiling point (°C./mm Hg) |
|---|---|---|---|---|---|---|---|
| 74 | 2,3-Cl₂-C₆H₃ | CH₃ | H | H | H | —(CH₂)₃— | 129/0,1 (cis) |
| 75 | 2-F-C₆H₄ | —CH₂-2-F-C₆H₄ | H | H | C₂H₅ | —(CH₂)₅— | 160/0,1 (cis) |
| 76* | CH₃ / 2-CH₃-C₆H₄ | CH₃ | H | H (CH₃) | CH₃ (H) | —(CH₂)₄— | 114/0,1 (cis)* |
| 77* | 2-Cl-C₆H₄ | CH₃ | H | H (CH₃) | CH₃ (H) | —(CH₂)₄— | 127/0,2 (cis)* |
| 78* | 2-F-C₆H₄ | CH₃ | H | H (C₂H₅) | C₂H₅ (H) | —(CH₂)₄— | 122/0,2 (cis)* |
| 79* | 2-CH₃-C₆H₄ | CH₃ | H | H (C₂H₅) | C₂H₅ (H) | —(CH₂)₄— | 127/0,1 (cis)* |
| 80 | 2-F-C₆H₄ | —CH₂-2-F-C₆H₄ | H | H | C₂H₅ | —(CH₂)₄— | 166/0,1 (cis) |
| 81* | 2-F-C₆H₄ | H | H | H (C₂H₅) | C₂H₅ (H) | —(CH₂)₄— | 115/0,3 (cis)* |
| 82 | 2-CH₃-C₆H₄ | —CH₂-2-CH₃-C₆H₄ | H | H | C₂H₅ | —(CH₂)₄— | 168/0,1 (cis) |
| 83 | 2,3-Cl₂-C₆H₃ | —CH₂-2,3-Cl₂-C₆H₃ | H | H | C₂H₅ | —(CH₂)₄— | 220–25/0,1 (cis) |
| 84* | 2-CH₃-C₆H₄ | H | H | H (C₂H₅) | C₂H₅ (H) | —(CH₂)₄— | 124/0,2 (cis)* |
| 85* | 2,3-Cl₂-C₆H₃ | CH₃ | H | H (C₂H₅) | C₂H₅ (H) | —(CH₂)₄— | 152/0,1 (cis)* |
| 86 | 2-F-C₆H₄ | —CH₂-2-F-C₆H₄ | H | H | C₆H₅ | —(CH₂)₄— | 210/0,1 (cis) |
| 87* | 2-F-C₆H₄ | CH₃ | H | H (C₆H₅) | C₆H₅ (H) | —(CH₂)₄— | 144/0,1 (cis)* |
| 88* | 2-F-C₆H₄ | C₂H₅ | H | H (C₆H₅) | C₆H₅ (H) | —(CH₂)₄— | 152/0,1 (cis)* |

TABLE 1-continued $$\begin{array}{c} Y^1 \quad X \\ | \quad | \\ C-O-CH-R^1 \\ A \Big| \\ C-O-R^2 \\ | \\ Y^2 \end{array} \quad (I)$$

| Ex. No. | R¹ | R² | X | Y¹ | Y² | A | Boiling point (°C./mm Hg) |
|---|---|---|---|---|---|---|---|
| 89* | Cl-C₆H₄- | H | H | H (C₆H₄) | (C₆H₄) (H) | —(CH₂)₄— | 154/0,1 (cis)* |
| 90 | F-C₆H₄- | F-C₆H₄-CH₂- | H | H | H | —CH₂—CH=CH—CH₂— | 140/0,2 (cis) |
| 91 | Cl-C₆H₄- | CH₃ | H | H | H | —CH₂—CH=CH—CH₂— | 145/0,3 (cis) |
| 92 | Cl-C₆H₄- | Cl-C₆H₄-CH₂- | H | H | H | —CH₂—CH=CH—CH₂— | 195/0,3 (cis) |
| 93 | CH₃-C₆H₄- | CH₃ | H | H | H | —CH₂—CH=CH—CH₂— | 160/0,2 (cis) |
| 94 | CH₃-C₆H₄- | CH₃-C₆H₄-CH₂- | H | H | H | —CH₂—CH=CH—CH₂— | 180/0,2 (cis) |
| 95* | Cl-C₆H₄- | CH₃ | H | H (C₆H₄) | C₆H₅ (H) | —(CH₂)₄— | 158/0,1 (cis)* |
| 96 | Cl-C₆H₄- | Cl-C₆H₄-CH₂- | H | H | C₆H₅ | —(CH₂)₄— | 226/0,1 (cis) |
| 97 | PhO-C₆H₄- | PhO-C₆H₄-CH₂- | H | H | C₆H₅ | —(CH₂)₄— | 290/0,1 (cis) |
| 98 | Cl-C₆H₄- | CH₃ | H | H | H | —(CH₂)₆— | 130/0,1 (trans) |
| 99 | Cl₂-C₆H₃- | CH₃ | H | H | H | —(CH₂)₆— | 160/0,1 (trans) |
| 100* | Cl₃-C₆H₂- | CH₃ | H | H (C₆H₄) | C₆H₅ (H) | —(CH₂)₄— | 200/0,1 (cis)* |
| 101* | PhO-C₆H₄- | CH₃ | H | H (C₆H₄) | C₆H₅ (H) | —(CH₂)₄— | 250/0,1 (cis)* |
| 102 | Cl-C₆H₄- | CH₃ | H | H | H | —(CH₂)₆— | 122/0,1 (cis) |
| 103 | F-C₆H₄- | CH₃ | H | H | H | —(CH₂)₆— | 111/0,1 (cis) |

TABLE 1-continued $$\underset{Y^2}{\overset{Y^1}{\underset{|}{C}}}\text{—O—}\overset{X}{\underset{|}{CH}}\text{—}R^1 \quad (I)$$
$$A\overset{|}{\underset{|}{C}}\text{—O—}R^2$$

| Ex. No. | R[1] | R[2] | X | Y[1] | Y[2] | A | Boiling point (°C./mm Hg) |
|---|---|---|---|---|---|---|---|
| 104 | 3,4-Cl₂-C₆H₃ | CH₃ | H | H | H | —(CH₂)₅— | 118/0,09 (cis) |
| 105 | 2-Cl-C₆H₄ | CH₃ | H | H | H | —(CH₂)₃— | 115/0,13 (cis) |
| 106 | 2-CH₃-C₆H₄ | CH₃ | H | H | H | —CH₂—(CHBr)₂—CH₂— | 195/0,2 (cis) |
| 107* | 2-F-C₆H₄ | CH₃ | H | H | C₆H₅ (H) | —(CH₂)₂— | $n_D^{25}=1,5465$ (cis)* |
| 108 | 2-F-C₆H₄ | —CH₂—C≡CH | H | H | H | —(CH₂)₄— | 101/0,2 (cis/trans) |
| 109 | 2-Cl-C₆H₄ | C₂H₅ | H | H | H | —CH₂—CH=CH—CH₂— | 101/0,2 (cis) |
| 110 | 2-F-C₆H₄ | —CH₂—(2-F-C₆H₄) | H | H | H | —(CH₂)₂— | 165/0,2 (cis/trans) |
| 111 | 2-Cl-C₆H₄ | —CH₂—(2-Cl-C₆H₄) | H | H | H | —(CH₂)₂— | 175/0,2 (cis/trans) |
| 112 | 2-CH₃-C₆H₄ | —CH₂—(2-CH₃-C₆H₄) | H | H | H | —(CH₂)₂— | 180/0,2 (cis/trans) |
| 113 | 2-F-C₆H₄ | —CH₂—(2-F-C₆H₄) | H | H | H | —(CH₂)₄— | 170/0,2 (cis/trans) |
| 114 | 2-Cl-C₆H₄ | —CH₂—(2-Cl-C₆H₄) | H | H | H | —(CH₂)₄— | 190/0,3 (cis/trans) |
| 115 | 2-CH₃-C₆H₄ | —CH₂—(2-CH₃-C₆H₄) | H | H | H | —(CH₂)₄— | 195/0,2 (cis) |
| 116 | 2-Cl-C₆H₄ | —CH₂—(2-Cl-4-F-C₆H₃) | H | H | H | —(CH₂)₃— | 161/0,1 (cis) |
| 117 | 2-F-C₆H₄ | —(CH₂)₃—CH₃ | H | H | H | —(CH₂)₃— | 106/0,2 (cis) |

TABLE 1-continued $$\underset{Y^2}{\overset{Y^1}{\underset{|}{A}\underset{|}{\overset{|}{C}}}}\underset{C-O-R^2}{\overset{X}{\overset{|}{C-O-CH-R^1}}} \quad (I)$$

| Ex. No. | R¹ | R² | X | Y¹ | Y² | A | Boiling point (°C./mm Hg) |
|---|---|---|---|---|---|---|---|
| 118 | Cl—⌬—F | —CH₃ | H | H | H | —(CH₂)₃— | 103/0,2 (cis) |
| 119 | Cl—⌬—F | C₂H₅ | H | H | H | —(CH₂)₃— | 108/0,2 (cis) |
| 120 | F—⌬ | —CH₂—CH=CH₂ | H | H | H | —(CH₂)₃— | 99/0,1 (cis) |
| 121 | F—⌬ | —(CH₂)₂—CH₃ | H | H | H | —CH₂)₃— | 101/0,2 (cis) |
| 122 | F—⌬ | —CH₂—C≡CH | H | H | H | —(CH₂)₃— | 110/0,1 (cis) |
| 123 | Cl—⌬—F | CH₃ | H | H | H | —(CH₂)₅— | 102/0,06 (cis) |
| 124 | F—⌬ | C₂H₅ | H | H | H | —(CH₂)₅— | 108/0,01 (cis) |
| 125 | Cl—⌬ | CH₃ | H | H | H | —(CH₂)₃—CH(—⌬)— | 156–62/0,1 (cis) |
| 126 | Cl—⌬ | CH₃ | H | H | H | —(CH₂)₃—CH(—(CH₂)₂—CH(CH₃)₂)— | 138/1,0 (cis) |
| 127 | CH₃—⌬ | CH₃ | H | H | H | —(CH₂)₃—CH(—⌬)— | 144/0,1 (cis) |
| 128 | F—⌬ | CH₃ | H | H | H | —(CH₂)₃—CH(—⌬)— | 139–43/0,09 (cis) |
| 129 | F—⌬ | n-C₃H₇ | H | H | H | —(CH₂)₅— | 111/0,1 (cis) |
| 130 | Cl—⌬ | n-C₃H₇ | H | H | H | —(CH₂)₅— | 129/0,1 (cis) |
| 131 | ⌬ | CH₃ | H | H | H | —CH₂)₅— | 92/0,1 (cis) |
| 132 | F—⌬ | n-C₆H₁₃ | H | H | H | —(CH₂)₃— | 124/0,1 (cis) |

TABLE 1-continued $$\underset{Y^2}{\overset{Y^1}{\underset{|}{C}}}-O-\overset{X}{\underset{|}{C}H}-R^1 \quad (I)$$
$$A\Big\langle \underset{|}{\overset{|}{C}}-O-R^2$$

| Ex. No. | R¹ | R² | X | Y¹ | Y² | A | Boiling point (°C./mm Hg) |
|---|---|---|---|---|---|---|---|
| 133 | phenyl | —CH₂—phenyl | H | H | H | —(CH₂)₃— | 137/0,1 (cis) |
| 134 | phenyl | —CH₂—phenyl | H | H | H | —(CH₂)₅— | 150/0,1 (cis) |
| 135 | CH₃-phenyl | CH₃-phenyl-CH₂— | H | H | H | —(CH₂)₃— | 155/0,1 (cis) |
| 136 | F-phenyl | n-C₇H₁₅ | H | H | H | —CH₂)₃— | 140/0,1 (cis) |
| 137 | F-phenyl | n-C₈H₁₇ | H | H | H | —CH₂)₃— | 136/0,07 (cis) |
| 138 | CH₃O-phenyl | CH₃ | H | H | H | —(CH₂)₃— | 121/0,2 (cis) |
| 139 | Cl-phenyl | n-C₃H₇ | H | H | H | —(CH₂)₃— | 117/0,1 (cis) |
| 140 | Cl-phenyl | —CH₂—CH=CH₂ | H | H | H | —(CH₂)₃— | 122/0,1 (cis) |
| 141 | CH₃O-phenyl | CH₃ | H | H | H | —(CH₂)₅— | 132/0,09 (cis) |
| 142 | Cl-phenyl | C₂H₅ | H | H | H | —(CH₂)₃— | 112/0,25 (cis) |
| 143 | phenyl | CH₃-phenyl-CH₂— | H | H | H | —(CH₂)₄— | 155–60/0,2 (cis) |
| 144 | phenyl | F-phenyl-CH₂— | H | H | H | —(CH₂)₄— | 165–70/0,2 (cis) |
| 145 | phenyl | Cl-phenyl-CH₂— | H | H | H | —(CH₂)₄— | 175/0,2 (cis) |

*Mixtures of position isomers (position isomers with respect to Y¹ and Y²)

It will be understood that the specification and examples are illustrative but not limitative of the present invention and that other embodiments within the spirit and scope of the invention will suggest themselves to those skilled in the art.

What is claimed is:

1. Benzyl ether of cyclic 1,2-diols, of the formula

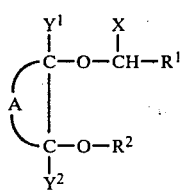

wherein
R¹ is phenyl or substituted phenyl, which substituents are selected from the group consisting of halogen, alkyl, alkoxy with up to 4 carbon atoms, haloalkyl, haloalkoxy with up to 4 carbon atoms each and up to 5 halogen atoms, trimethylene, tetramethylene or pentamethylene groups, and phenyl, and phenoxy, the last two radicals being optionally substituted by halogen, alkyl or alkoxy with 1 to 2 carbon atoms each or haloalkyl with up to 2 carbon atoms and up to 3 identical or different halogen atoms;

$R^2$ is alkyl with 1 to 8 carbon atoms, alkenyl or alkynyl with 2 to 4 carbon atoms each, haloalkyl with up to 2 carbon atoms and up to 3 identical or different halogen atoms or the grouping —CHX—$R^1$ wherein X is defined as below;

X is hydrogen, alkyl with 1 to 4 carbon atoms, alkenyl, or alkynyl with 2 to 4 carbon atoms, haloalkyl with up to 2 carbon atoms and up to 3 identical or different halogen atoms, phenyl or substituted phenyl, the substituents being selected from halogen, alkyl or alkoxy with 1 or 2 carbon atoms each or haloalkyl with up to 2 carbon atoms and up to 3 identical or different halogen atoms;

$Y^1$ and $Y^2$ are individually selected from hydrogen, alkyl with 1 to 6 carbon atoms or phenyl or substituted phenyl, the substituents being selected from halogen, alkyl or alkoxy with 1 to 4 carbon atoms or haloalkyl or haloalkoxy with up to 4 carbon atoms each and up to 5 halogen atoms and A is a 2- or 6-membered saturated or unsaturated alkyllene bridge or substituted alkylene bridge, the substituents being slected from halogen, alkyl with 1 to 6 carbon atoms, phenyl and substituted phenyl, the substituents being selected from halogen, alkyl or alkoxy with up to 4 carbon atoms each, haloalkyl or haloalkoxy with up to 4 carbon atoms each and up to 5 halogen atoms each.

2. Benzyl ether as claimed in claim 1, wherein $R^1$ is phenyl.

3. Benzyl ether as claimed in claim 1, wherein $R^1$ is substituted phenyl.

4. Benzyl ether as claimed in claim 1, wherein $R^2$ is alkyl.

5. Benzyl ether as claimed in claim 1, wherein $R^2$ is alkenyl.

6. Benzyl ether as claimed in claim 1, wherein $R^2$ is haloalkyl.

7. Benzyl ether as claimed in claim 1, wherein $R^2$ is CHX-$R^1$.

8. Benzyl ether as claimed in claim 1, wherein X is hydrogen.

9. Benzyl ether as claimed in claim 1, wherein X is alkyl.

10. Benzyl ether as claimed in claim 1, wherein X is alkenyl.

11. Benzyl ether as claimed in claim 1, wherein X is haloalkyl.

12. Benzyl ether as claimed in claim 1, wherein X is phenyl.

13. Benzyl ether as claimed in claim 1, wherein X is substituted phenyl.

14. Benzyl ether as claimed in claim 1, wherein $Y^1$ and $Y^2$ are hydrogen.

15. Benzyl ether as claimed in claim 1, wherein $Y^1$ and $Y^2$ are alkyl.

16. Benzyl ether as claimed in claim 1, wherein $Y^1$ and $Y^2$ are phenyl or substituted phenyl.

17. Benzyl ether as claimed in claim 1, wherein one of $Y^1$ and $Y^2$ is hydrogen.

18. Benzyl ether as claimed in claim 1, wherein one of $Y^1$ and $Y^2$ is alkyl.

19. Benzyl ether as claimed in claim 1, wherein one of $Y^1$ and $Y^2$ is phenyl or substituted phenyl.

20. Benzyl ether as claimed in claim 1, wherein A is saturated alkylene.

21. Benzyl ether as claimed in claim 1, wherein A is unsaturated alkylene.

22. Benzyl ether as claimed in claim 1, wherein A is substituted alkylene.

23. Benzyl ether as claimed in claim 1, wherein A is a two-membered to six-membered saturated or unsaturated alkylene bridge which may carry at least one substituent selected from halogen, straight-chain or branched alkyl with 1 to 6 carbon atoms, phenyl and phenyl which is substituted by halogen, by alkyl or aloxy with in either case 1 to 4 carbon atoms, or by haloalkyl or haloalkoxy with in each case up to 4 carbon atoms and up to 5 halogen atoms;

$Y^1$ and $Y^2$, which are identical or different, each represent hydrogen, straight-chain or branched alkyl with 1 to 6 carbon atoms, phenyl or phenyl substituted by halogen, alkyl or alkoxy with 1 to 4 carbon atoms each or haloalkyl or haloalkoxy with in each case up to 4 carbon atoms and up to 5 halogen atoms;

X represents hydrogen, straight-chain or branched alkyl with 1 to 4 carbon atoms, alkenyl with 2 to 4 carbon atoms, haloalkyl with up to 2 carbon atoms and up to 3 identical or different halogen atoms or phenyl which is optionally substituted by halogen, alkyl or alkoxy with in either case 1 or 2 carbon atoms or haloalkyl with up to 2 carbon atoms and up to 3 identical or different halogen atoms; and $R^2$ represents straight-chain or branched alkyl with 1 to 4 carbon atoms, alkenyl with 2 to 4 carbon atoms, haloalkyl with up to 2 carbon atoms and up to 3 identical or different halogen atoms or the grouping —CHX—$R^1$ wherein $R^1$ and X have the meanings above set forth.

24. Benzyl ether, as claimed in claim 1, wherein said compound is cis-1-(2-fluorobenzyloxy)-2-methoxy-cyclobutane.

25. Benzyl ether, as claimed in claim 1, wherein said compound is cis-1-(2-fluorobenzyloxy)-2-methoxy-cyclohexane.

26. Benzyl ether as claimed in claim 1, wherein said compound is cis-1-(2-methylbenzyloxy)-2-methoxy-cyclobutane.

27. Benzyl ether, as claimed in claim 1, wherein said compound is cis-1-(2-bromobenzyloxy)-2-methoxy-cyclobutane.

28. Benzyl ether as claimed in claim 1, wherein said compound is cis-1-(2-fluorobenzyloxy)-2-ethoxy-cyclopentane.

* * * * *